(12) United States Patent
Pashley et al.

(10) Patent No.: US 12,187,624 B2
(45) Date of Patent: Jan. 7, 2025

(54) METHOD OF ACYLATING AMINO ACIDS AND USES OF N-ACYL AMINO ACID PRODUCTS

(71) Applicant: NewSouth Innovations Pty Limited, Sydney (AU)

(72) Inventors: Richard Mark Pashley, Sydney (AU); Mojtaba Taseidifar, Sydney (AU)

(73) Assignee: NewSouth Innovations Pty Limited, Sydney (AU)

( * ) Notice: Subject to any disclaimer, the term of this patent is extended or adjusted under 35 U.S.C. 154(b) by 516 days.

(21) Appl. No.: 17/431,891

(22) PCT Filed: Feb. 18, 2020

(86) PCT No.: PCT/AU2020/050142
§ 371 (c)(1),
(2) Date: Aug. 18, 2021

(87) PCT Pub. No.: WO2020/168385
PCT Pub. Date: Aug. 27, 2020

(65) Prior Publication Data
US 2023/0183095 A1    Jun. 15, 2023

(30) Foreign Application Priority Data
Feb. 18, 2019 (AU) ............................ 2019900519

(51) Int. Cl.
*C02F 1/24* (2023.01)
*C02F 101/36* (2006.01)
*C02F 103/06* (2006.01)

(52) U.S. Cl.
CPC ............ *C02F 1/24* (2013.01); *C02F 2101/36* (2013.01); *C02F 2103/06* (2013.01)

(58) Field of Classification Search
CPC ........................... C07C 231/00; C07C 233/47
See application file for complete search history.

(56) References Cited

U.S. PATENT DOCUMENTS 5,017,364 A    5/1991    Mitsutake et al.
5,981,450 A    11/1999    Fabry et al.
(Continued)

FOREIGN PATENT DOCUMENTS

WO        2018071985 A1    4/2018
WO    WO-2019169177 A1 *    9/2019

OTHER PUBLICATIONS

Bordes, R, et. al, Amino acid-based surfactants—do they deserve more attention? Advances in Colloid and Interface Science, 222 ( 2015) 79-91 (Year: 2015).*
(Continued)

*Primary Examiner* — Bradley R Spies
*Assistant Examiner* — Jeannie McDermott
(74) *Attorney, Agent, or Firm* — Myers Bigel, P.A.

(57) ABSTRACT

The present invention relates to a method of preparing N-acyl amino acids selected from N-acyl cysteine compounds, N-acyl serine compounds, N-acyl aspartic acid compounds and N-acyl glutamic acid compounds. The present invention also relates to the use of N-acyl cysteine, N-acyl serine, N-acyl aspartic acid and N-acyl glutamic acid surfactants, in removing per- and poly-fluoroalkyl substances (PFASs) from mixtures containing PFASs, such as soil and groundwater contaminated with PFASs and for use in cleaning compositions, detergent compositions and toothpaste compositions.

13 Claims, 5 Drawing Sheets

(56) References Cited

U.S. PATENT DOCUMENTS 9,987,207 B1 6/2018 Wang et al.
2021/0171365 A1* 6/2021 Nelson .................. C02F 1/24

OTHER PUBLICATIONS

Tripathy, D, et. al, Synthesis, chemistry, physicochemical properties and industrial applications of amino acid surfactants: A review, Comptes Rendus Chimie, 21 (2018) 112-130 (Year: 2018).*

"International Search Report and Written Opinion corresponding to International Application No. PCT/AU2020/050142 mailed Apr. 3, 2020".

Bordes, Romain, et al., "Amino acid-based surfactants—do they deserve more attention?", Advances in Colloid and Interface Science 222:79-91 (Mar. 28, 2015).

Erol, Kadir, et al., "Use of amino acid-based polymeric material for isolation of a protein from poison", Journal of Molecular Structure 1130:753-759 (2017).

Hur, Deniz, et al., "N-Acylbenzotriazole Mediated Synthesis of Some Methacrylamido Amino Acids", Letters in Organic Chemistry 4(8):585-587 (Sep. 24, 2007).

Jalilzadeh, Mitra, et al., "Specific heavy metal ion recovery with ion-imprinted cryogels", J. Appl. Polym. Sci. 133 (10):43095 (2016) (9 pages).

Katritzky, Alan R, et al., "Selective Synthesis and Structural Elucidation of S-Acyl- and N-Acylcysteines", J. Org. Chem. 74(18):7165-7167 (Aug. 21, 2009).

* cited by examiner

METHOD OF ACYLATING AMINO ACIDS AND USES OF N-ACYL AMINO ACID PRODUCTS

CROSS-REFERENCE TO RELATED APPLICATIONS

This application is a 35 U.S.C. § 371 national phase application of PCT Application PCT/AU20201050142, filed Feb. 18, 2020, which claims the benefit of priority of Australian provisional application No. 2019900519, filed Feb. 18, 2019, the entire contents of each of which are incorporated herein by reference in its entirety for all purposes.

FIELD OF THE INVENTION

The present invention relates to a method of preparing N-acyl amino acids selected from N-acyl cysteine compounds, N-acyl serine compounds, N-acyl aspartic acid compounds and N-acyl glutamic acid compounds. The method finds particular, though not exclusive, application in the preparation of N-acyl cysteine, N-acyl serine, N-acyl aspartic acid and N-acyl glutamic acid surfactants and will primarily be described in this context. As will be appreciated, the present invention may be applied to the preparation of a wide range of N-acyl cysteine compounds N-acyl serine compounds, N-acyl aspartic acid compounds and N-acyl glutamic acid compounds for a wide range of applications.

The present invention also relates to the use of N-acyl cysteine, N-acyl serine, N-acyl aspartic acid and N-acyl glutamic acid surfactants, including their use in removing per- and poly-fluoroalkyl substances (PFASs) from mixtures containing PFASs, such as soil and groundwater contaminated with PFASs.

BACKGROUND OF THE INVENTION

N-Acyl cysteine, N-acyl serine, N-acyl aspartic acid and N-acyl glutamic acid products have many uses. For example, N-acyl cysteines having longer acyl chains have been useful as surfactants. In WO 2018/071985, N-acyl cysteines having longer acyl chains were useful for removing heavy metals from aqueous solutions.

One problem that has hindered wider commercial use of N-acyl cysteines is the difficulty in obtaining N-acyl cysteines on a commercially useful scale. Underlying this problem is the low-yielding processes currently available for preparing N-acyl cysteines.

It would be advantageous to provide alternative methods of accessing N-acyl cysteines. N-acyl serines, N-acyl aspartic acids and N-acyl glutamic acids, especially methods that are efficient (i.e. high yielding), clean (i.e. minimal and/or easily removable by-products), operationally simple, and do not require difficult and/or time-consuming purification steps to deliver N-acyl cysteines, N-acyl serines, N-acyl aspartic acids and N-acyl glutamic acids in a form pure enough for subsequent use.

Per- and poly-fluoroalkyl substances (PFASs) have been widely used over the last 60 years or more for a range of applications, including in non-stick cookware, as water repellent coatings, stain resistant fabrics and carpets, some cosmetics and some products that resist grease, water, and oil. Notably, PFASs have been used in fire-fighting foams, especially for aviation fires, where they have been released into the environment, including into the groundwater surrounding airports. PFASs can travel long distances, move through soil, seep into groundwater or be carried through air. The release of PFASs into the environment has become an increasing concern as PFASs do not easily break down by natural processes. PFASs can persist for long periods in the environment and can be absorbed by humans or animals, where they may accumulate. Recent studies have reported that human exposure to PFASs is associated with adverse health effects. For example, studies have shown that PFASs affect growth, learning, and behavior of infants and older children; lower a woman's chance of getting pregnant; interfere with the body's natural hormones; increase cholesterol levels; affect the immune system; and increase the risk of cancer. The USEPA has recommended limits of 70 ng/L for these compounds in drinking water.

It would be advantageous to provide methods of removing PFASs from mixtures containing PFASs, such as soil or groundwater contaminated with PFASs.

SUMMARY OF THE INVENTION

In a first aspect, the present invention provides a method of preparing an N-acyl amino acid of Formula (I):

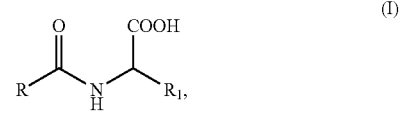

or a salt thereof, where R is selected from H, $C_1$-$C_{15}$ alkyl groups, $C_2$-$C_{15}$ alkenyl groups, $C_2$-$C_{15}$ alkynyl groups, fluorinated $C_1$-$C_{15}$ alkyl groups, fluorinated $C_2$-$C_{15}$ alkenyl groups and fluorinated $C_2$-$C_{15}$ alkynyl groups, and $R_1$ is selected from SH, OH, $CO_2H$ and $CH_2CO_2H$, the method comprising reacting cysteine, serine, aspartic acid or glutamic acid and an N-acylbenzotriazole of Formula (II):

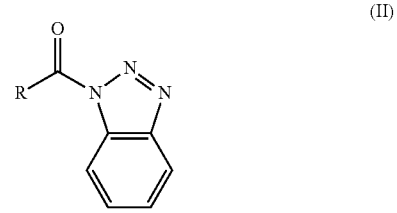

wherein R is as defined in Formula (I), in a solvent composed substantially of methanol.

In some embodiments, R is a linear or branched $C_5$-$C_{10}$ alkyl group. In some embodiments, R is a linear $C_6$-$C_9$ alkyl group. In some embodiments, $R_1$ is SH. In some embodiments, the solvent is at least 99% v/v methanol.

In a second aspect, the present invention provides an N-acyl cysteine, N-acyl serine, N-acyl aspartic acid or N-acyl glutamic acid of Formula (I) or a salt thereof prepared by the method of the first aspect.

In a third aspect, the present invention provides a method of removing one or more PFASs from an aqueous phase comprising one or more PFASs, the method comprising dissolving in the aqueous phase a foaming agent of Formula (Ia):

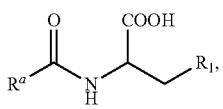

(Ia)

or a salt thereof,
wherein $R^a$ is a $C_5$-$C_{12}$ alkyl group, a $C_5$-$C_{12}$ alkenyl group, a $C_5$-$C_{12}$ alkynyl group, a fluorinated $C_5$-$C_{12}$ alkyl group, a fluorinated $C_5$-$C_{12}$ alkenyl group or a fluorinated $C_5$-$C_{12}$ alkynyl group;
$R_1$ is SH, OH, $CO_2H$ or $CH_2CO_2H$;
forming a foam from the aqueous phase and a gas; and
separating the foam from the aqueous phase.

In some embodiments, $R^a$ is a $C_6$-$C_9$ alkyl group. In some embodiments, $R_1$ is SH. In particular embodiments, the foaming agent of formula (Ia) is in a salt form. In some embodiments, the foaming agent of Formula (Ia) or salt thereof has a solubility of greater than 0.0001 M in water. In some embodiments, the Critical Micelle Concentration (CMC) of the foaming agent of Formula (Ia) or salt thereof in the aqueous phase is greater than 0.0001 M. In some embodiments, the concentration of the foaming agent of Formula (Ia) or salt thereof in the aqueous phase is from about 0.01 mM to about 2 M, for example, from about 0.01 mM to about 0.02 M or from about 0.01 mM to about 0.2 M. In some embodiments, the concentration of the foaming agent of Formula (Ia) or salt thereof in the aqueous phase is from about 0.0001 M to about 2 M, for example, from about 0.0001 mM to about 0.02 M or from about 0.0001 mM to about 0.2 M. In some embodiments, the one or more PFASs comprises at least one PFAS capable of binding to a multivalent metal ion. In some embodiments, the aqueous phase has a pH within the range of from about pH 4 to about pH 12. In some embodiments, the aqueous phase comprises one or more metal ions selected from $Ca^{2+}$, $Mg^{2+}$, $Al^{3+}$ and $Fe^{3+}$. In some embodiments, the aqueous phase comprises PFAS-contaminated soil or PFAS-contaminated groundwater.

In a fourth aspect, the present invention provides the use of a foaming agent of Formula (Ia):

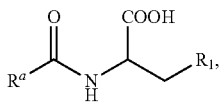

(Ia)

or a salt thereof,
where $R^a$ is a $C_5$-$C_{12}$ alkyl group, a $C_5$-$C_{12}$ alkenyl group, a $C_5$-$C_{12}$ alkynyl group, a fluorinated $C_5$-$C_{12}$ alkyl group, a fluorinated $C_5$-$C_{12}$ alkenyl group or a fluorinated $C_5$-$C_{12}$ alkynyl group;
$R_1$ is SH, OH, $CO_2H$ or $CH_2CO_2H$;
for removing one or more PFASs from an aqueous phase.

In some embodiments, the foaming agent of Formula (Ia) or salt thereof is used in a foam fractionation process to remove the one or more PFASs from the aqueous phase. In some embodiments, $R^a$ is a $C_6$-$C_9$ alkyl group. In some embodiments, $R_1$ is SH. In particular embodiments, the foaming agent of formula (Ia) is in a salt form. In some embodiments, the foaming agent of Formula (Ia) or salt thereof has a solubility of greater than 0.0001 M in water. In some embodiments, the CMC of the foaming agent of Formula (Ia) or salt thereof in the aqueous phase is greater than 0.0001 M. In some embodiments, the aqueous phase comprises PFAS-contaminated soil or PFAS-contaminated groundwater.

In some embodiments, there is provided a cleaning composition, detergent composition or toothpaste composition comprising an N-acyl amino acid of Formula (I), or a salt thereof, where R is selected from a $C_5$-$C_{12}$ alkyl group, a $C_5$-$C_{12}$ alkenyl group and a $C_5$-$C_{12}$ alkynyl group and $R_1$ is SH, OH, $CO_2H$ or $CH_2CO_2H$.

BRIEF DESCRIPTION OF THE FIGURES

Particular embodiments of the present invention are described below, by way of example only, with reference to the accompanying drawings in which.

DETAILED DESCRIPTION OF THE INVENTION

Figure 1:
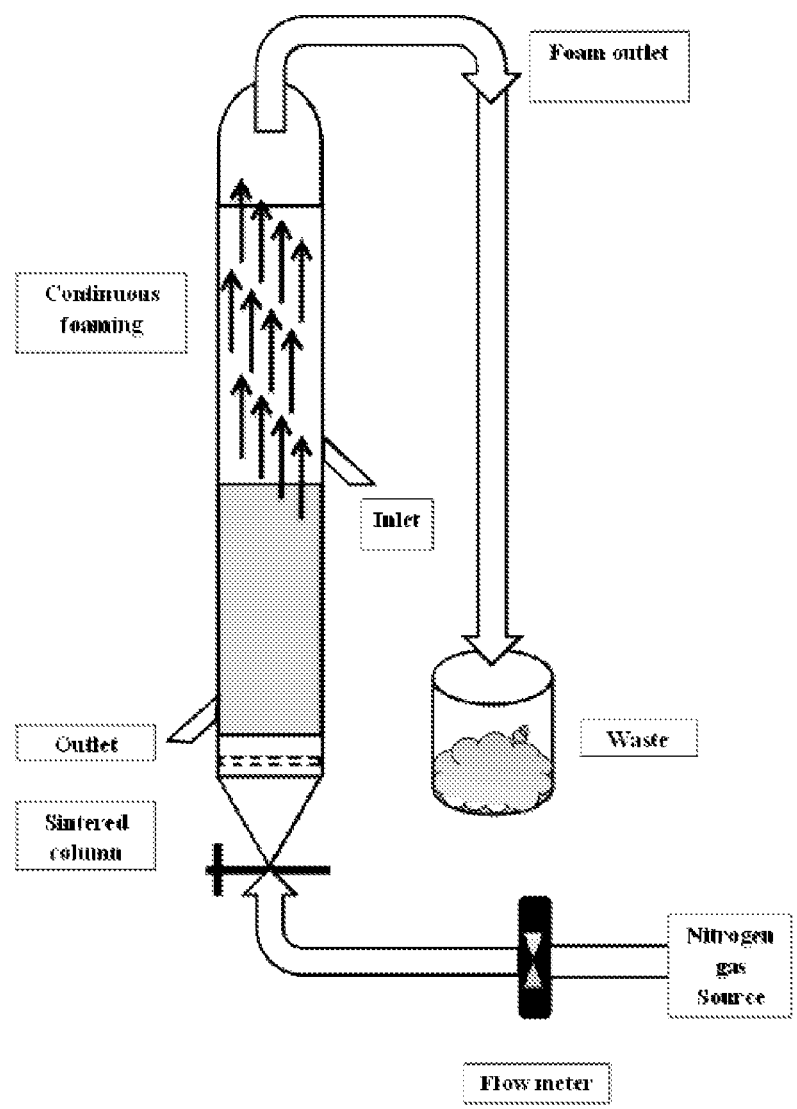
FIG. 1 is a schematic representation of a column apparatus suitable for carrying out the method of the third aspect of the present invention.

Particular embodiments of the present invention are described below, by way of example only.

In a first aspect, the present invention provides a method of preparing an N-acyl amino acid of Formula (I):

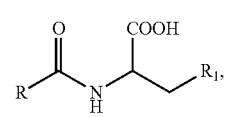

(I)

or a salt thereof,
where R is selected from H, $C_1$-$C_{15}$ alkyl groups, $C_2$-$C_{15}$ alkenyl groups, $C_2$-$C_{15}$ alkynyl groups, fluorinated $C_1$-$C_{15}$ alkyl groups, fluorinated $C_2$-$C_{15}$ alkenyl groups and fluorinated $C_2$-$C_{15}$ alkynyl groups, and $R_1$ is SH, OH, $CO_2H$ or $CH_2CO_2H$;

the method comprising reacting cysteine and an N-acyl-benzotriazole of Formula (II):

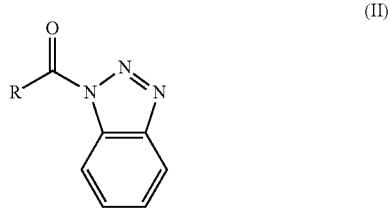

(II)

wherein R is as defined in Formula (I), in a solvent composed substantially of methanol.

In some embodiments, R is H. In such embodiments, the reaction may be referred to as a "formylation" reaction. In other embodiments (e.g. where R is a $C_1$-$C_{15}$ alkyl group) the reaction may be referred to as an "acylation" reaction.

The term "alkyl" refers to a straight chain or branched chain saturated hydrocarbyl group. The term "$C_{1-15}$ alkyl" refers to an alkyl group having 1 to 15 carbon atoms. Similarly, "$C_{5-12}$ alkyl" refers to an alkyl group having 5 to 12 carbon atoms. Examples of linear alkyl groups include methyl, ethyl, n-propyl, n-butyl, n-pentyl, n-hexyl, n-heptyl, n-octyl, n-nonyl, n-decyl, n-undecyl and n-dodecyl and the like. Examples of branched alkyl groups include 2-methylpropyl, 2-methylbutyl, 3-methylbutyl, 2,2-dimethylpropyl, 2-methylpentyl, 3-methylpentyl, 4-methylpentyl, 2,2-dimethylbutyl, 2,3-dimethylbutyl, 2-ethylbutyl, 2-methylhexyl, 3-methylhexyl, 4-methylhexyl, 5-methylhexyl, 2,2-dimethylpentyl, 3,3-dimethylpentyl, 2,3-dimethylpentyl, 2,4-dimethylpentyl, 3,4-dimethylpentyl, 2-ethylpentyl, 3-ethylpentyl and the like.

The term "alkenyl" refers to a straight chain or branched chain hydrocarbyl group having at least one double bond of either E- or Z-stereochemistry where applicable. The term "$C_{2-15}$ alkenyl" refers to an alkenyl group having 2 to 15 carbon atoms. Similarly, "$C_{5-12}$ alkenyl" refers to an alkenyl group having 5 to 12 carbon atoms. In some embodiments, the alkenyl group contains more than one double bond, for example 2, 3, 4, 5 or 6 double bonds. The alkenyl group may, in addition to the one or more double bonds, also contain one or more triple bonds. Examples of alkenyl include vinyl, 1-propenyl, 1- and 2-butenyl, 2-methyl-2-propenyl, 2- and 3-butenyl, 2-, 3- and 4-pentenyl, 2-, 3-, 4- and 5-hexenyl, 2-, 3-, 4-, 5- and 6-heptenyl, 2-, 3-, 4-, 5-, 6- and 7-octenyl, 3-methyl-6-octenyl and the like.

The term "alkynyl" refers to a straight chain or branched chain hydrocarbyl group having at least one triple bond. The term "$C_{2-15}$ alkynyl" refers to an alkynyl group having 2 to 15 carbon atoms. Similarly, "$C_{5-12}$ alkynyl" refers to an alkynyl group having 5 to 12 carbon atoms. In some embodiments, the alkynyl group contains more than one triple bond, for example 2, 3, 4, 5 or 6 triple bonds. The alkynyl group may, in addition to the one or more triple bonds, also contain one or more double bonds. Examples of alkynyl include ethynyl, 1-propynyl, 1- and 2-butynyl, 2-, 3- and 4-pentynyl, 2-, 3-, 4- and 5-hexynyl, 2-, 3-, 4-, 5- and 6-heptynyl, 2-, 3-, 4-, 5-, 6- and 7-octynyl, 3-methyl-6-octynyl and the like.

The teen "fluorinated" refers to a group such as an alkyl, alkenyl or alkynyl group defined above, in which one or more hydrogen atoms in the relevant group are replaced with one or more fluorine atoms and includes instances where all of the hydrogen atoms are replaced with fluorine atoms. Functional groups where all of the hydrogen atoms have been replaced with fluorine are referred to as "perfluorinated". In some embodiments, the fluorinated group contains one fluorine atom. In other embodiments, the fluorinated group contains more than one fluorine atom (e.g., 2, 3, 4, 5, 6, 7, 8, 9, 10, 11, 12, 13, 14, 15, 16, 17, 18, 19, 20, 21, 22, 23, 24, 25 fluorine atoms), as permitted by the valency of the relevant group. Examples of fluorinated alkyl groups include —$CH_2F$, —$CHF_2$, —$(CH_2)CF_2CH_3$, —$(CH_2)_5CF_3$ and —$(CF_2)_6CH_3$. Examples of perfluorinated sibyl groups include —$CF_3$, —$C_6F_{13}$, —$C_7F_{15}$ and —$C_8F_{17}$.

In some embodiments, $R_1$ is SH and the compound of formula (I) is a N-acyl cysteine. In other embodiments, $R_1$ is is OH and the compound of formula (I) is a N-acyl serine. In yet other embodiments, $R_1$ is $CO_2H$ and the compound of formula (I) is a N-acyl aspartic acid. In yet other embodiments, $R_1$ is $CH_2CO_2H$ and the compound of formula (I) is a N-acyl glutamic acid. In particular embodiments, $R_1$ is SH and the compound of formula (I) is a N-acyl cysteine having the formula:

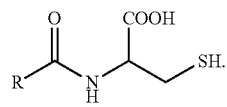

In some embodiments, R is branched (e.g. a branched $C_3$-$C_{15}$ alkyl group, a branched $C_3$-$C_{15}$ alkenyl group or a branched $C_5$-$C_{15}$ alkynyl group). Due to steric considerations, when R is branched, the α-carbon (i.e. the carbon alpha to the carbonyl of the acyl group) is preferably $CH_2$ (i.e. the α-carbon is preferably not the site of branching in the branched group). As a person skilled in the art will appreciate, acyl groups having substituted α-carbons may be affected by steric effects during the reaction, leading to a less facile reaction.

In some embodiments, R contains from 1 to 15 carbon atoms (i.e. is a $C_1$-$C_{15}$ group). Examples include a $C_2$-$C_{10}$ group, a $C_2$-$C_5$ group, a $C_3$-$C_{15}$ group, a $C_3$-$C_{10}$ group, a $C_3$-$C_5$ group, a $C_4$-$C_{15}$ group, a $C_4$-$C_{10}$ group, a $C_4$-$C_8$ group, a $C_4$-$C_6$ group, a $C_5$-$C_{15}$ group, a $C_5$-$C_{10}$ group or a $C_5$-$C_8$ group. In some embodiments, R contains 1 carbon atom. In some embodiments, R contains 2 carbon atoms. In some embodiments, R contains 3 carbon atoms. In some embodiments, R contains 4 carbon atoms. In some embodiments, R contains 5 carbon atoms. In some embodiments, R contains 6 carbon atoms. In some embodiments, R contains 7 carbon atoms. In some embodiments, R contains 8 carbon atoms. In some embodiments, R contains 9 carbon atoms. In some embodiments, R contains 10 carbon atoms. In some embodiments, R contains 11 carbon atoms. In some embodiments, R contains 12 carbon atoms. In some embodiments, R contains 13 carbon atoms. In some embodiments, R contains 14 carbon atoms. In some embodiments, R contains 15 carbon atoms.

In some embodiments, R is selected from linear $C_1$-$C_{15}$ alkyl groups, linear $C_2$-$C_{15}$ alkenyl groups, linear $C_2$-$C_{15}$ alkynyl groups, fluorinated linear $C_1$-$C_{15}$alkyl groups, fluorinated linear $C_2$-$C_{15}$ alkenyl groups, fluorinated linear $C_2$-$C_{15}$ alkynyl groups, branched $C_3$-$C_{15}$ alkyl groups, branched $C_3$-$C_{15}$ alkenyl groups, branched $C_4$-$C_{15}$ alkynyl groups, fluorinated branched $C_3$-$C_{15}$ alkyl groups, fluorinated branched $C_3$-$C_{15}$ alkenyl groups, fluorinated branched $C_4$-$C_{15}$ alkynyl groups. In some particular embodiments, R is a linear $C_6$-$C_9$ alkyl group, especially the $C_7$ alkyl group. In some particular embodiments, R is n-heptyl (—$C_7H_{15}$), and the product is therefore N-octyl cysteine, N-octyl serine, N-octyl aspartic acid or N-octyl glutamic acid.

In some particular embodiments, R is methyl (—$CH_3$), and the product is therefore N-acetyl cysteine.

In some embodiments, the R group of the N-acyl amino acid of Formula (I) is hydrophobic. In such embodiments, the N-acyl amino acid of Formula (I) may perform as an N-acyl amino acid surfactant. Advantageously, when the R group is sufficiently hydrophobic, the product N-acyl amino acid has poor solubility in solvents composed substantially on methanol. As a result, the product may precipitate from the solution and be collected by filtration techniques. Advantageously, the reaction typically produces minimal by-products, so the precipitated product may not need further purification or only need washing/rinsing with a suitable solvent (e.g. ethanol or acetone) to provide N-acyl cysteine. N-acyl serine, N-acyl aspartic acid or N-acyl glutamic acid product having a useful purity. In some embodiments, the yield is greater than 90% (e.g. greater than 95%, greater than 97% or greater than 98%). Also advantageously, the benzotriazole by-product typically remains in solution after the reaction and may be recycled to prepare more N-acylbenzotriazole for use in the method. For example, the benzotriazole-containing by product may be soluble in methanol or acetone. Therefore, rinsing the product N-acyl cysteine, N-acyl serine, N-acyl aspartic acid or N-acyl glutamic acid with acetone may keep the benzotriazole-containing by-product in solution, allowing the separation, for example, filtration, from the N-acyl cysteine, N-acyl serine, N-acyl aspartic acid or N-acyl glutamic acid product. The dissolved benzotriazole-containing by-product may then be recovered, for example, by removal of solvent under reduced pressure, and subsequently used.

Cysteine, serine, aspartic acid and glutamic acid are four of the twenty common amino acids and are readily commercially available in both stereoisomers. As will be appreciated, the natural stereoisomer of cysteine (i.e. L-cysteine), serine (L-serine), aspartic acid (L-aspartic acid) and glutamic acid (L-glutamic acid) may be more readily available and are typically cheaper to purchase from commercial suppliers. The stereochemistry of the cysteine, serine, aspartic acid and glutamic acid in the present invention is not particularly limited, and the choice may be dependent on the desired use of the N-acyl amino acid product. In some embodiments, the amino acid is L-cysteine, L-serine, L-aspartic acid or L-glutamic acid. In other embodiments, the amino acid is D-cysteine, D-serine, D-aspartic acid or D-glutamic acid. For large scale applications where stereochemistry is not important, L-cysteine, L-serine, L-aspartic acid or L-glutamic acid may be preferred to minimize costs. In some embodiments, the amino acid may be in the form of a racemic mixture (D/L)

The method of the present invention comprises reacting an amino acid selected from cysteine, serine, aspartic acid and glutamic acid, and an N-acylbenzotriazole of Formula (II):

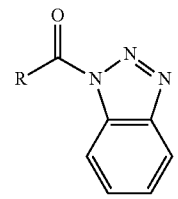

For the avoidance of doubt, the R group of the N-acylbenzotriazole of Formula (II) corresponds to the R group of the N-acyl amino acid product of Formula (I). Therefore, R in Formula (II) is selected from H, linear $C_1$-$C_{15}$ alkyl groups, $C_2$-$C_{15}$ alkenyl groups, $C_2$-$C_{15}$ alkynyl groups, fluorinated $C_1$-$C_{15}$ alkyl groups, fluorinated $C_2$-$C_{15}$ alkenyl groups and fluorinated $C_2$-$C_{15}$ alkynyl groups as defined above for Formula (I). Accordingly, the R group of the N-acylbenzotriazole of Formula (II) will be selected according to the R group of the desired N-acyl amino acid product of Formula (I).

Various N-acylbenzotriazoles are commercially available. Various syntheses of various N-acylbenzotriazoles have also been reported. For example, a convenient procedure to access a variety of N-acylbenzotriazoles, from the corresponding carboxylic acid, has been reported (Katritzky et al., *Synthesis*, 2003, 3, 2795-2798). As a person skilled in the art will appreciate, a wide range of N-acylbenzotriazoles may be purchased or prepared using this, and/or other, reported procedures.

The reaction between an amino acid selected from cysteine, serine, aspartic acid and glutamic acid, and the N-acylbenzotriazole takes place "in a solvent composed substantially of methanol". In this context, "in a solvent" refers to the medium in which the reaction occurs (i.e. where the cysteine, serine, aspartic acid or glutamic acid and N-acylbenzotriazole are able to make contact and react). In the present context, "composed substantially of methanol" refers to the composition of the solvent, which is at least 80% v/v methanol (e.g. at least 90% v/v, at least 95% v/v, at least 98% v/v, at least 99% v/v or at least 99.5% v/v methanol). The balance of the solvent may be a co-solvent selected from suitable inert solvents that allow the cysteine to dissolve, and do not react with the N-acylbenzotriazole to any appreciable extent. Examples of co-solvents include ethanol, propanol and isopropanol. The reaction may, in some embodiments, tolerate small amounts of contaminants in the solvent. The methanol does not necessarily need to be rigorously dried. However, the methanol typically contains less than about 1 wt. % water as the presence of water may affect the reaction yield. The reaction typically performs better (e.g. higher yield, less by-products) when there is no, or at least minimal, water in the solvent. Accordingly, in some embodiments, the solvent contains less than 1 wt. % water, for example, less than 0.5 wt. %, less than 0.2 wt. %, less than 0.1 wt. %, less than 0.05 wt %, less than 0.02 wt. % or less than 0.01 wt. % water. In some embodiments, methanol is used (as the solvent or co-solvent) as supplied without any further purification or drying. In some embodiments, methanol is dried prior to use as the solvent or co-solvent (e.g. by passage or storage over 3 angstrom molecular sieves). Persons skilled in the art are aware of various methods of drying methanol.

It is believed that it is important that at least a portion of the amino acid selected from cysteine, serine, aspartic acid and glutamic acid (preferably a significant portion of the cysteine, serine, aspartic acid and glutamic acid, if not all of the cysteine, serine, aspartic acid and glutamic acid) dissolves in the solvent for the reaction to proceed at a practical rate. It is believed that a major drawback to previous methods was that in previous methods the cysteine was not sufficiently soluble in the solvent, which would slow or inhibit any reaction from occurring. Previously (e.g. WO 2018/071985), appreciable amounts of water were required to facilitate the dissolution of cysteine; however, solvents having appreciable water content proved to be incompatible with the acylating agents used (e.g. acid chlorides), leading to low yields of the desired product.

The present invention is predicated, at least in part, on the discovery of cysteine being sufficiently soluble in a solvent/solvent system which is simultaneously compatible with a class of acylating agents that do not react to any appreciable extent with the solvent/solvent system, and that are also soluble (at least to a useful extent) in the solvent/solvent system.

The method of the present invention does not need to be performed at any particular temperature, so long as the solvent is in the liquid state. A person skilled in the art will be able to choose an appropriate temperature, and may adjust the temperature to take account of differing reaction rates (e.g. depending on the nature of the N-acylbenzotriazole). The temperature does not need to be static and can be changed during the reaction. In some embodiments, the reaction of cysteine, serine, aspartic acid or glutamic acid, and N-acylbenzotriazole is performed at a temperature in the range of from about 10° C. to about 65° C. (the boiling point of methanol), from about 10° C. to about 50° C., from about 15° C. to about 30° C. or from about 20° C. to about 25° C. Advantageously, the reaction may, in some embodiments, proceed at a practical rate at ambient temperature, avoiding the need for heating or cooling and thereby reducing manufacturing costs.

The method comprises reacting cysteine, serine, aspartic acid or glutamic acid and an N-acylbenzotriazole in a solvent composed substantially of methanol. In some embodiments, the N-acylbenzotriazole is added neat to a solution of cysteine, serine, aspartic acid or glutamic acid. In some embodiments, the N-acylbenzotriazole is in a solution which is added to a solution of cysteine, serine, aspartic acid or glutamic acid. In some embodiments, the cysteine, serine, aspartic acid or glutamic acid is added neat to a solution of N-acylbenzotriazole. In some embodiments, the cysteine, serine, aspartic acid or glutamic acid is in a solution which is added to a solution of N-acylbenzotriazole. In some embodiments, the addition is in a single batch. In other embodiments, the addition is portion-wise (e.g. dropwise) over a period of time. In some embodiments, the reaction mixture is mechanically agitated (e.g. stirred) before, during and/or after the cysteine, serine, aspartic acid and glutamic acid and the N-acylbenzotriazole are combined.

The N-acyl amino acid of Formula (I) may be prepared as a salt, where an H atom ($H^+$ ion) of the α-COOH group is replaced by another cation, for example $Na^+$. For example, the sodium salt of N-octanoyl cysteine, N-octanoyl serine, N-octanoyl aspartic acid or N-octanoyl glutamic acid has the following structure:

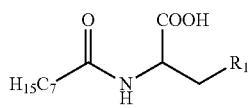

wherein $R_1$ is SH, OH, $CO_2H$ or $CH_2CO_2H$.

In some embodiments, where the amino acid is aspartic acid or glutamic acid, the side chain carboxylic acid may also be in the form of a salt, for example, a disodium salt having the following stricture:

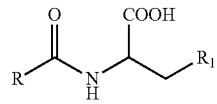

wherein $R_1$ is $CO_2Na$ or $CH_2CO_2Na$.

Examples of suitable salts also include salts of Na, K, Li or Cs. Methods of converting carboxylic acids to carboxylate salts are known (e.g. selective precipitation, cation exchange columns etc.) and a person skilled in the art will be able to determine an appropriate method. Salt forms of formula (I) are particularly useful in surfactants.

In a second aspect, the present invention provides an N-acyl amino acid of Formula (I) or a salt thereof prepared by the method of the first aspect.

In some embodiments, the present invention provides the use of an N-acyl amino acid of Formula (I) or a salt thereof prepared by the method of first aspect.

In some embodiments, the N-acyl amino acid of formula (I) is N-acyl cysteine, N-acyl serine or N-acyl aspartic acid. In some embodiments, the N-acyl amino acid of formula (I) is N-acyl cysteine or N-acyl serine. In some embodiments, the N-acyl amino acid of formula (I) is N-acyl cysteine.

Applications of N-Acyl Amino Acids of Formula (I)

Advantageously, the method of the present invention provides access to N-acyl cysteines of Formula (I) having free thiol groups (—SH). Free thiol groups are reported to have antioxidant effects and are reportedly useful in the harvesting of free radicals in cells, leading to a number of potential therapeutic uses of N-acyl cysteines of Formula (I) where $R_1$ is SH, prepared by the method of the first aspect of the present invention. In some embodiments, the N-acyl amino acid is in free acid form. For example, N-acetyl cysteine has been reported to participate in general antioxidant activities of the body (Sansone et al. *Innov. Clin. Neurosci.* 2011:8(1): 10-14) and may be implicated in a number of diseases. Accordingly, in some embodiments there is provided a method of treating psychiatric disorders allegedly related to oxidative stress (e.g. schizophrenia, bipolar disorder) and/or psychiatric syndromes characterized by impulsive/compulsive symptoms (e.g. trichotillomania, pathological nail biting, gambling, substance misuse), by administration to a patient in need of treatment of an N-acyl cysteine of Formula (I) where $R_1$ is SH (e.g. N-acetyl cysteine) prepared by the method of the first aspect of the present invention.

N-acyl amino acids of Formula (I) including N-acyl cysteines, N-acyl serines, N-acyl aspartic acids or N-acyl glutamic acids, and salts thereof, are, in some embodiments, believed to be biocompatible. Further, in some embodiments, at least some of the decomposition products are also believed to be biocompatible. As such, in some embodiments, the present invention provides the use of an N-acyl cysteine, N-acyl serine. N-acyl aspartic acid or N-acyl glutamic acid of Formula (I), especially foaming agents of Formula (Ia), more especially where R is a $C_5$-$C_{12}$ alkyl group, a $C_5$-$C_{12}$ alkenyl group or a $C_5$-$C_{12}$ alkynyl group, as a replacement for surfactants such as sodium dodecyl sulfate (SDS) or sodium lauryl sulfate (SLS) in detergents/cleaners or toothpastes. In this regard, SDS and SLS have reported health and environmental concerns. Accordingly, in some embodiments there is provided a cleaning composition, detergent composition or toothpaste composition comprising an N-acyl amino acid of Formula (I) or a salt thereof, where R is selected from a $C_5$-$C_{12}$ alkyl group, a $C_5$-$C_{12}$ alkenyl group and a $C_5$-$C_{12}$ alkynyl group. In some particular embodiments, the N-acyl amino acid of Formula (I) or a salt thereof, where R is selected from a $C_5$-$C_{12}$ alkyl group, a $C_5$-$C_{12}$ alkenyl group and a $C_5$-$C_{12}$ alkynyl group, is prepared by the method of the first aspect of the present invention.

In some embodiments, the N-acyl amino acid is a N-acyl cysteine. In other embodiments, the N-acyl amino acid is N-acyl serine. In yet other embodiments, the N-acyl amino acid is N-acyl aspartic acid. In still other embodiments, the N-acyl amino acid N-acyl glutamic acid. In particular embodiments, the N-acyl amino acid is N-acyl cysteine. In some embodiments, the N-acyl amino acid is in a salt form.

Methods of Removing PFAS

In a third aspect, the present invention provides a method of removing one or more PFASs from an aqueous phase containing one or more PFASs, the method comprising dissolving in the aqueous phase a foaming agent of Formula (Ia):

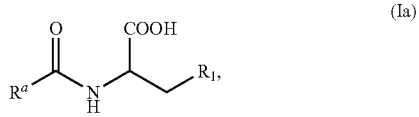

or a salt thereof,
wherein $R_1$ is SH, OH, $CO_2H$ or $CH_2CO_2H$; and
$R^a$ is a $C_5$-$C_{12}$ alkyl group, a $C_5$-$C_{12}$ alkenyl group, a $C_5$-$C_{12}$ alkynyl group, a fluorinated $C_5$-$C_{12}$ alkyl group, a fluorinated $C_5$-$C_{12}$ alkenyl group or a fluorinated $C_5$-$C_{12}$ alkynyl group;
forming a foam from the aqueous phase and a gas; and
separating the foam from the aqueous phase.

As used herein, "PFASs" refers to per- and poly-fluoroalkyl substances. Examples of PFASs include perfluorooctane sulfonate, also known as "PFOS"; and perfluorooctanoic acid, also known as "PFOA". Perfluorohexane sulfonate (PFHxS) is another chemical of the PFAS group and is present in some fire-fighting foams. In some embodiments, the PFAS is a PFAS capable of binding to a multivalent cation, such as $Ca^{2+}$, $Mg^{2+}$, $Al^{3+}$ and $Fe^{3+}$. Examples include per- or polyfluoro $C_1$-$C_{20}$ alkanoic acids, per- or polyfluoro $C_1$-$C_{20}$ alkyl sulfonates.

As used herein, "removing one or more PFASs" refers to the removal of at least a portion of at least one PFAS, thus reducing the amount or concentration of at least one PFAS in the aqueous phase. In some embodiments, at least 50% (e.g. at least 80%, at least 90%, at least 95%, at least 98%, or at least 99%) of one type or species of PFAS is removed. In some embodiments, at least 50% (e.g. at least 80%, at least 90%, at least 95%, at least 98%, or at least 99%) of the entire content of PFASs is removed. In some embodiments, the one or more PFASs comprises at least one PFAS capable of binding to a multivalent metal ion, such as $Ca^{2+}$, $Mg^{2+}$, $Al^{3+}$ or $Fe^{3+}$.

The method comprises dissolving a foaming agent of Formula (Ia) or a salt thereof in an aqueous phase containing one or more PFASs. A reference herein to an "aqueous phase" refers to a phase in which water is the only solvent or is at least 50% (e.g. at least 80%, at least 90%, at least 95%, at least 98%, or at least 99%) by weight of the total solvent. As will be appreciated, the aqueous phase may contain other solid components (such as soil) and/or contaminants. Preferably, water comprises at least 90%, at least 95%, at least 98%, or at least 99%, by weight of the total solvents in the aqueous phase.

The aqueous phase may be any aqueous phase comprising one or more PFASs. The aqueous phase may, for example, be groundwater or waste water from an industrial process, mining or other human activity, comprising one or one or more PFASs. In some embodiments, metal ions are added prior to performing the method. In some embodiments, the aqueous phase is or comprises PFAS-contaminated groundwater. The aqueous phase may comprise particulates. In some embodiments, the aqueous phase comprises PFAS-contaminated soil. In such embodiments, the soil may, for example, represent from about 1% to about 95% w/w of the aqueous phase, e.g. from about 10% to about 50% w/w of the aqueous phase. When forming a foam, the gas may, for example, occupy from about 1% to about 95% v/v of the total volume (the total volume including the gas, the aqueous phase and the soil). For example, in some embodiments, the gas occupies from about 20% to about 90% v/v of the total volume. In some embodiments, the soil represents from about 5% to about 90% v/v of the total volume, such as from about 10% to about 80% v/v or from about 20% to about 60% v/v of the total volume. In some embodiments, the aqueous phase is an aqueous phase that has been used to rinse contaminated soil (e.g. an aqueous phase that has been in contact with contaminated soil). In some embodiments, the aqueous phase contains soil contaminated with one or more PFASs. Typically, the aqueous phase does not contain large amounts of materials (e.g. insoluble oils, polydimethylsiloxanes and other silicones, certain alcohols, stearates and glycols) which will inhibit the foaming agent of Formula (Ia) from facilitating the formation of foam from the aqueous phase.

Advantageously, in some embodiments, foaming agents of Formula (Ia) are capable of forming foams over a broad range of pHs. For example, N-octanoyl cysteine may form a foam at a pH of from about 3 to about 12. Accordingly, in some embodiments, the pH of the aqueous phase to be treated is in the range of from about pH 3 to about pH 12 (e.g. from about pH 4 to about pH 10, from about pH 4 to about pH 8, from about pH 5 to about pH 7). Advantageously, foaming agents of Formula (Ia) are typically capable of forming foams at pHs resembling groundwater.

In some embodiments, the aqueous phase comprises one or more metal ions in addition to the one or more PFASs. Examples of metal ions include multivalent metal ions such as $Ca^{2+}$, $Mg^{2+}$, $Al^{3+}$ or $Fe^{3+}$. In some embodiments, the metal ions are added to the aqueous phase prior to treatment. In some embodiments, the metal ions are already present in the aqueous phase to be treated. In some embodiments, additional metal ions are added, before or during treatment, to an aqueous phase which already contains metal ions. In such embodiments, the added metal ions may be the same or different to those already in the aqueous phase. Examples of metal ions useful in the present invention include multivalent cations capable of forming bridges, such as cations of Ca, Mg, Al and Fe (e.g. $Ca^{2+}$, $Mg^{2+}$, $Al^{3+}$ and $Fe^{3+}$), especially Ca. Advantageously, Ca is prevalent in soil and groundwater, which can obviate the need to add additional metal ions to the aqueous phase before treatment.

The concentration of metal ions in the aqueous phase is not particularly limited. In some embodiments, the concentration of metal ions is equal to or greater than the concentration of the foaming agent of Formula (Ia) dissolved in the aqueous phase. In some embodiments, the concentration of metal ions is selected to minimise the wastage of the foaming agent of Formula (Ia). In some embodiments, the concentration of metal ion in the aqueous phase is greater than 0.0001 M, e.g. greater than 0.001 M, 0.01 M or 0.1 M. For example, from about 0.0001 M to about 2 M or from about 0.0001 M to about 0.02 M.

In some embodiments, the foaming agent of Formula (Ta) or salt thereof is prepared by the method of the first aspect or is derived from a compound of Formula (I) prepared by the method of the first aspect.

In some embodiments of the foaming agent of Formula (Ia), $R_1$ is SH, In other embodiments, $R_1$ is OH. In yet other embodiments, $R_1$ is $CO_2H$. In still other embodiments, $R_1$ is $CH_2CO_2H$. In particular embodiments, $R_1$ is SH, OH or $CO_2H$, especially SH or OH and more especially SH.

In the foaming agent of Formula (Ia), $R^a$ is preferably hydrophobic. In some embodiments, $R^a$ is linear. In some embodiments, $R^a$ is branched. In some embodiments, $R^a$ is an alkyl group. In some embodiments, $R^a$ is an alkenyl group. In some embodiments, $R^a$ is an alkynyl group. In some embodiments, $R^a$ is a fluorinated alkyl group. In some embodiments, $R^a$ is a fluorinated alkenyl group. In some embodiments, $R^a$ is a fluorinated alkynyl group. In some embodiments, $R^a$ is $C_6$-$C_9$ group. In some embodiments, $R^a$ is a $C_6$-$C_8$ group. In some embodiments, $R^a$ is a $C_7$ group. In some particular embodiments, $R^a$ is a linear $C_5$-$C_{10}$ alkyl group, especially a linear $C_6$-$C_8$ alkyl group, more especially n-heptyl (—$C_7H_{15}$). In some particular embodiments, $R^a$ is a fluorinated linear $C_5$-$C_{10}$ alkyl group, especially a fluorinated linear $C_6$-$C_8$ alkyl group, more especially a fluorinated n-heptyl (e.g. perfluorinated n-heptyl, —$C_7F_{15}$).

As used herein, a "foaming agent" is a material, typically a surfactant, which facilitates the formation of foam from an aqueous phase. When gas passes through the aqueous phase, typically as small bubbles, the foaming agent facilitates the formation of a foam. The "foaming agent of Formula (Ia) or salt thereof" is therefore a compound of Formula (Ia) or a salt thereof which facilitates the formation of a foam from an aqueous phase. In particular embodiments of foaming agent, the N-acyl amino acid is in salt form. In some embodiments, the foaming agent of Formula (Ia) or salt thereof contains a cysteine group and acts as a surfactant. It is therefore sometimes referred to as a "cysteine surfactant". In other embodiments, the foaming agent of Formula (Ia) or salt thereof contains a serine group and acts as a surfactant. It is therefore sometimes referred to as a "serine surfactant". In yet other embodiments, the foaming agent of Formula (Ia) or salt thereof contains an aspartic acid group and acts as a surfactant. It is therefore sometimes referred to as a "aspartic acid surfactant". In still other embodiments, the foaming agent of Formula (Ia) or salt thereof contains a glutamic acid group and acts as a surfactant. It is therefore sometimes referred to as a "glutamic acid surfactant".

Surfactants are compounds that lower the surface tension (or interfacial tension) between two liquids or between a liquid and a solid. Surfactants are usually organic compounds that are amphiphilic, meaning they contain both a hydrophobic group (their tail) and a hydrophilic group (their head). Therefore, a surfactant contains both a water-insoluble or oil-soluble component and a water-soluble component (typically a polar group and/or a group capable of carrying a charge). Surfactants will diffuse in water and adsorb at interfaces between air and water or at the interface between oil and water, in the case where water is mixed with oil. The water-insoluble hydrophobic group may extend out of the bulk water phase, into the air or into the oil phase, while the water-soluble head group remains in the water phase. In some embodiments, the PFAS may act as a surfactant. In such embodiments, the PFAS and the foaming agent of Formula (Ia) or salt thereof may each act as co-surfactants.

The foaming agent is capable of facilitating the formation of a foam from the aqueous phase, that is, facilitating the formation of a foam comprising pockets of a gas encapsulated by the aqueous phase. For example, after the gas is passed through the aqueous phase, typically in the form of small bubbles (e.g. having a diameter of about 1 mm to about 10 mm), bubbles of the gas move to the surface of the aqueous phase to form a foam on the surface. Typically, the gas bubbles are allowed to rise to the top of the aqueous phase to form a foam layer. The foam layer phase can then be separated from the aqueous phase thereby isolating the PFASs (present in the foam layer) from the aqueous phase. The foam may be separated by any means which separates the foam (containing the adsorbed PFASs) from the bulk aqueous phase. In some embodiments, the foam forms a foam layer on top of the bulk aqueous phase and the foam layer is wiped away (e.g. displaced with a paddle or similar). In some embodiments, the foam is removed under negative pressure (e.g. by suction through a tube). In some embodiments, the foam is removed using a positive pressure (e.g. by being pushed or extruded through an outlet). The foam can, for example, be separated from the liquid phase using au outlet tube to collect the foam in a waste container (e.g. exiting the bubble column in FIG. 2 through the "Foam outlet" and into the "Waste"). The collected foam comprising the PFAS may be collapsed prior to disposal, for example, using silicone or ethanol sprays. In some embodiments, a foam breaker is used to collapse the foam. In some embodiments, a mechanical foam breaker, such as a defoaming pump or ultrasonic foam breaker, is used to collapse the foam. In some embodiments, the PFAS is isolated from the foam and/or the collapsed foam. In some embodiments, the foam may be treated to isolate the PFAS from the foam.

The method of the present invention may, for example, comprise aeration at a low flow-rate (e.g. 3 L/min through a sinter of about 7 $cm^2$ in area) of an aqueous phase containing the PFAS and the foaming agent of Formula (Ia) or a salt thereof in a suitable vessel, e.g. a bubble column. In such embodiments, as the aeration is performed, bubbles rise to the surface of the aqueous phase forming a foam on the surface which is then separated from the aqueous phase. Additional volume of an aqueous solution containing the PFAS, with or without the cysteine surfactant, may be introduced into the vessel. The additional aqueous phase introduced into the vessel (the feed solution) may be introduced into the vessel in a manner such that the feed solution is initially contacted with the foam so that some amount of separation of the PFAS from the feed solution takes place while it is passing through the foam. Alternatively, the feed solution could also be added directly to the aqueous phase below the interface of the aqueous phase and the foam, e.g. just below the foam.

Figure 5:
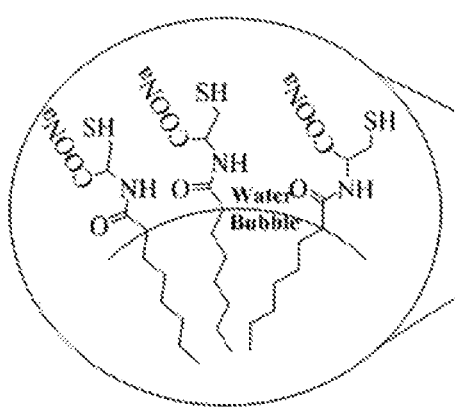
FIG. 5 is a schematic representation of the presumed orientation of the foaming agent around a bubble.

The foaming agent of Formula (Ia) or salt thereof dissolved in the aqueous phase forms a monolayer around the bubbles of the gas. The orientation of the foaming agent of Formula (Ia) or salt thereof around the bubble is such that the hydrophobic group (i.e. $R^a$) orients towards the gas and the polar head-group orients towards the aqueous phase (as shown for cysteine in FIG. 5). Bubbles passing through the aqueous phase provide a continuous supply of amino acid coated monolayers, where the surfactants and head-groups will be relatively mobile at room temperature (e.g. at 25° C.). It is believed that collisions between the PFAS species and the N-acyl amino acid coated bubbles provide a mechanism by which the cysteine can capture the PFAS, allowing the capture and removal of PFAS in a one-step treatment process. In embodiments where the aqueous phase comprises one or more metal ions, collisions between the metal ions, PFAS species and the N-acyl amino acid coated bubbles provide a mechanism by which the N-acyl amino acid such as N-acyl cysteine can assist in the capture and removal of PFAS. In this system, the polar head groups effectively chelate with metal ions in the aqueous phase, and facilitate the adsorption of PFASs into the bubble surface as a surfactant or co-surfactant. Without wishing to be bound by theory, it is believed that the fluid nature of the adsorbed surfactant layer at a bubble surface, which moves through the aqueous solution, supports an efficient spatial arrangement of groups to incorporate PFAS molecules, optionally via chelation with one or more metal ions. Once adsorbed, the PFAS and/or PFAS/metal ion complex can be effectively removed by the bubbles into a foam on the surface of the aqueous phase.

In the bulk aqueous phase, surfactants form aggregates, such as micelles, at concentrations above the critical micelle concentration (CMC), where the hydrophobic tails form the core of the aggregate and the hydrophilic heads are in contact with the surrounding liquid. The CMC of a surfactant in an aqueous phase can be determined by a person skilled in the art using techniques known in the art. For example, the CMC of a surfactant can be determined by measuring changes in the conductance or surface tension of the solution at different concentrations of the surfactant.

Preferably the foaming agent of Formula (Ia) or salt thereof has a solubility of greater than 0.0001 M in water, e.g. greater than 0.001 M or 0.01 M, at 25° C. For foaming agents of Formula (Ia) or salts thereof having a solubility in water below 0.0001 M, only low concentrations can be dissolved in an aqueous phase and this may limit the rate at which the PFASs can be removed from the aqueous phase.

Preferably, the CMC of the foaming agent of Formula (Ia) or salt thereof in the aqueous phase is greater than 0.0001 M, e.g. greater than 0.001 M or 0.01 M. In some embodiments, the CMC of the foaming agent of Formula (Ia) or salt thereof in the aqueous phase is from 0.0001 M to 1 M. In some embodiments, the CMC of the foaming agent of Formula (Ia) or salt thereof in water at 25° C. and atmospheric pressure is greater than 0.0001 M, e.g. greater than 0.001 M or 0.01 M. In some embodiments, the CMC of the foaming agent of Formula (Ia) or salt thereof in water at 25° C. and atmospheric pressure is from 0.0001 M to 1 M. Preferably, the foaming agent of Formula (Ia) or a salt thereof, is dissolved in the aqueous solution in an amount up to the CMC, that is, it is preferred that the foaming agent is dissolved in the aqueous phase in an amount to provide a concentration of the foaming agent below the CMC of the foaming agent. This is preferred as, if the concentration of the foaming agent exceeds the CMC, the foaming agent may form aggregates, such as micelles, and some of the PFASs and metal ions (if present) may become bound with the aggregates rather than the cysteine groups in the mono-layer around the bubbles of the gas passing through the aqueous phase. This may reduce the efficiency of the method of the present invention in removing the PFASs from the aqueous phase. However, in some embodiments, it may be possible to use amino acid surfactants such as cysteine surfactants at concentrations well above their CMC, for example, up to 1-2M or more, limited only by its solubility.

The method comprises forming a foam from the aqueous phase and a gas. When the aqueous phase comprises the dissolved foaming agent of Formula (Ia), the foaming agent will facilitate the formation of a foam. The foam may be formed by introducing the gas into the aqueous phase. The gas may be any gas that is substantially non-reactive with the foaming agent and the aqueous phase. The gas may, for example, be selected from the group consisting of air such as dry air or humidified air, carbon dioxide, nitrogen, oxygen, helium or argon.

In some embodiments, the aqueous phase is agitated to form the foam. In some embodiments the agitation is mechanical mixing (e.g. with a blade). In some embodiments the agitation is by aeration, such as by spraying a portion of the aqueous phase into another portion of the aqueous phase.

In some particular embodiments, the foam is formed by passing a gas through the aqueous phase. Accordingly, the present invention provides a method for a roving PFASs from an aqueous phase comprising one or more PFASs, the method comprising dissolving in the aqueous phase a foaming agent of Formula (Ia):

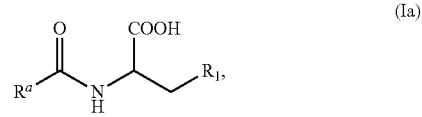

(Ia)

or a salt thereof, wherein $R_1$ is SH, OH, $CO_2H$ or $CH_2CO_2H$; and $R^a$ is a $C_5$-$C_{12}$ alkyl group, a $C_5$-$C_{12}$ alkenyl group, a $C_5$-$C_{12}$ alkynyl group, a fluorinated $C_5$-$C_{12}$ alkyl group, a fluorinated $C_5$-$C_{12}$ alkenyl group or a fluorinated $C_5$-$C_{12}$ alkynyl group;

passing a gas through the aqueous phase to form a foam; and separating the foam from the aqueous phase.

In some embodiments, the gas is passed through the aqueous solution to form a foam by bubbling the gas through the aqueous phase. In some embodiments, the gas is introduced into the aqueous phase near the base of the aqueous phase (e.g. near the floor of a vessel holding the aqueous phase) to form bubbles (typically having a diameter in the range of about 1 mm to about 10 mm) which rise through the aqueous phase to form a foam on the upper surface of the aqueous phase. The gas is typically passed through a porous material, for example, a porous glass or metal sinter, to form multiple bubbles of the gas in the aqueous phase. In some embodiments, the aqueous phase comprises one or more metal ions in addition to the one or more PFASs.

Without wishing to be bound by theory, it is believed that as the bubbles of the gas pass though the aqueous phase, a mono-layer of the foaming agent of Formula (Ia) is formed around each bubble of the gas. It is believed that, in some embodiments, it is the interaction between one or more of the cysteine groups, which extend from the surface of the bubble, with a metal ion, such as $Ca^{2+}$ (present in abundance in soil and groundwater), which results in the metal ion being bound by the cysteine group. In relation to contaminated soils and groundwater, it has been reported that PFASs, especially those that are negatively charged, may be bound to charged particles of sand, clay and humic acid coated materials and microorganisims via bridging multivalent ions (e.g. $Ca^{2+}$). It is reasoned that, in some embodiments, the foaming agents of Formula (Ia) bind the multi valent metal ions and displace the PFASs which are bound, via bridging multi-valent ions, to the charged particles of sand, clay and humic acid coated materials. The displaced PFASs may then associate (e.g. through hydrophobic attraction forces, fluorine-fluorine interactions, fluorine-π interactions, London dispersion forces, etc.) with the foaming agent of Formula (Ia), and thus facilitate the removal of the PFAS from the aqueous phase. Additionally, when a metal ion is captured by the cysteine group of the foaming agent of Formula (Ia), it could also foreseeably associate with a PFAS, especially a PFAS comprising a functional group which associates with metal ions (such as a carboxylate, sulfonate or other organic acid). Having associated with one PFAS (comprising a functional group which associates with a metal ion), the associated PFAS compound may then associate with other PFASs which do not contain a functional group known to bind to metal ions (for example through fluorine-fluorine interactions, fluorine-n interactions, London dispersion forces, hydrophobic attraction forces etc.). Accordingly, a wide range of PFASs may be removed by this method.

In most soils. $Ca^{2+}$ constitutes over 90% of total cation (Rieuwerts et al., *Chemical Speciation & Bioavailability*, 1998, 10, 61-75). Without wishing to be bound by theory, it is believed that $Ca^{2+}$ attaches to PFAS compounds (which may be present as contamination in soil), particularly PFAS compounds that are negatively charged. N-octanoyl-amino acid surfactants such as N-octanoyl cysteine surfactant may release PFAS compounds attached to the contaminated soil and act as a co-surfactant in foam cleaning/removal.

As gas bubbles pass through an aqueous phase, the PFASs (including PFASs that are bound to metal ions) become adsorbed onto the polar head groups of the mono-layer of the foaming agent of Formula (Ia) formed around each rising bubble. The bubbles then fora a foam comprising the adsorbed PFASs (including PFASs that are bound to metal ions), acting as a surfactant or co-surfactant, which can then be separated from the aqueous phase. Continuation of sparging until foaming ceases can be used to remove residual foaming agent from the aqueous phase as the presence of even low levels of the foaming agent causes foaming.

Advantageously, the foaming agent of Formula (Ia) may be broken down/decomposed to environmentally benign components, such as cysteine, serine, aspartic acid and glutamic acid, and $C_6$-$C_{13}$ alkanoic acids. The $R^a$ group may be chosen such that the resultant alkanoic acid has minimal environmental impact. This may be important in embodiments where complete removal of the foaming agent of Formula (Ia) may be difficult and/or not feasible (e.g. where method is used to treat large amounts of soil/groundwater). Accordingly, it may be viable to return the treated wastewater to the environment without completely removing the foaming agent of Formula (Ia) and without having environmental consequences.

Also advantageously, the method can be carried out with low energy consumption and small space requirements, which does not require the use of expensive technology, and which can be conducted in a one step process and/or at the point of access to the contaminated water or soil. Further still, the method can be carried out in a batch process or, advantageously, a continuous process. A continuous process can be advantageous as a continuous process is generally more energy and cost efficient for treating large volumes of an aqueous phase than a batch process.

Figure 2:
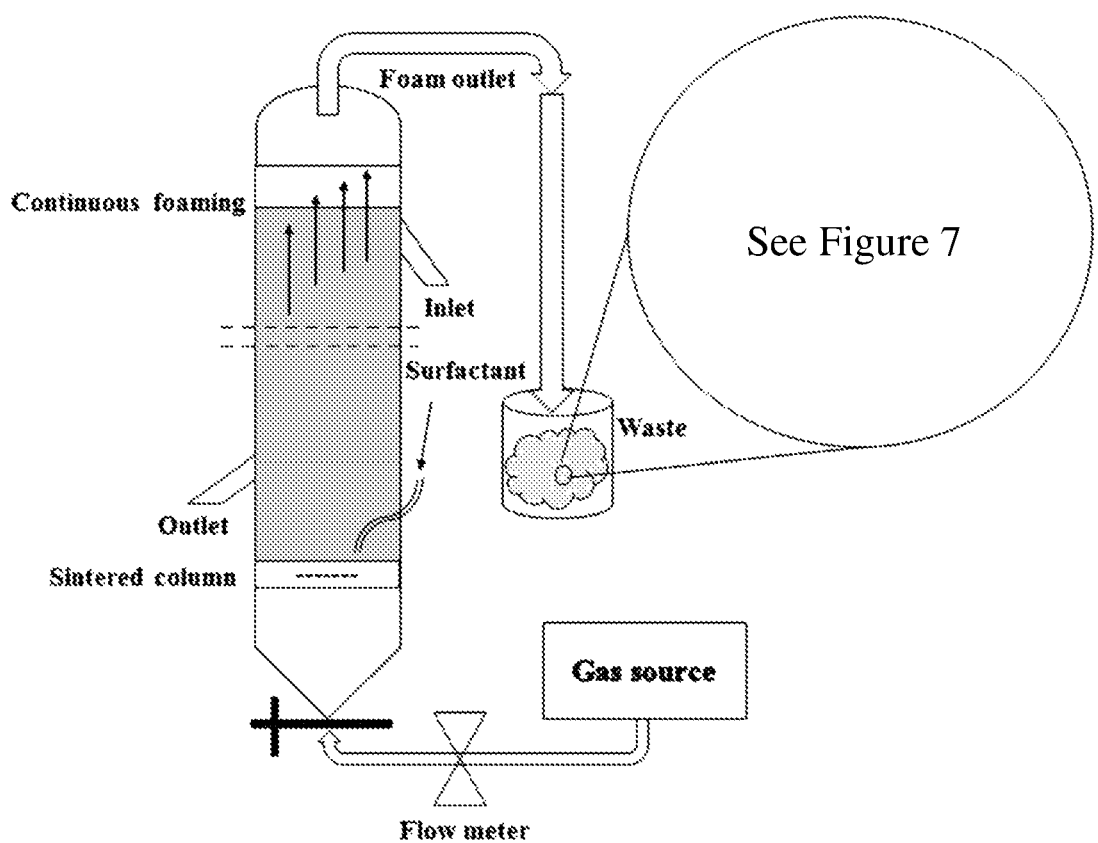
FIG. 2 is a schematic representation of another example of a column apparatus suitable for carrying out the method of the third aspect of the present invention. An expanded view of the waste container is shown in FIG. 7.

FIG. 1 is a schematic diagram of the column apparatus used in the experiments described in Example 2. The same or similar apparatus can, for example, be used to perform the method of the present invention in a batch process or a continuous process. For example, in a batch process, a sample of the aqueous phase may be treated in the column depicted in FIG. 1 and then the treated aqueous phase is removed from the column through the outlet. Following this, a new sample of the aqueous phase and the foaming agent is introduced to the column through the inlet for treatment by the method of the present invention. Similar apparatus can also be used in a continuous process. FIG. 2 depicts one example of suitable apparatus for carrying out the method of the present invention in a continuous process. Using the apparatus depicted in FIG. 2, the aqueous phase (feed solution) is introduced to the bubble column in a continuous flow through the inlet, and the treated aqueous solution removed through the outlet in a continuous flow. A concentrated solution of the foaming agent is introduced in a continuous flow through a separate inlet (labeled "Surfactant" in FIG. 2), positioned near to the sinter of the column. To provide a longer period of contact between the rising bubbles and the aqueous solution, the height of the column, relative to its other dimensions, will typically be greater than that depicted in FIG. 2. The outlet in FIG. 2 is orientated in a downward direction to avoid bubbles rising through the aqueous solution moving though the outlet as the aqueous solution is removed from the column. As a person skilled in the art will appreciate, various other apparatuses are possible for performing the method of the present invention.

Adsorptive bubble separation techniques have been used to remove various substances from wastewaters. There are several separation techniques employing adsorption on gas bubbles; these methods are divided into two categories, foam separation and non-foaming adsorptive bubble separation techniques. Foam separation techniques can be sub-divided into foam fractionation and flotation methods. Flotation methods include ion flotation, ore flotation, macro flotation, colloidal flotation and precipitate flotation. Ion flotation is a separation technology for recovering and removing metal ions from aqueous phases based on the association between the ions and a surfactant species. The ion and surfactant are adsorbed onto the surface of rising bubbles and carried into a foam on the surface, which is then removed from the solution. Foam fractionation methods preferentially separate hydrophobic molecules from a liquid solution using columns of foam.

The present invention may therefore provide a novel foam fractionation technique for removing PFASs from an aqueous phase.

In a fourth aspect, the present invention provides the use of a foaming agent of Formula (Ia):

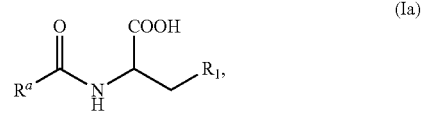
(Ia)

or a salt thereof,
wherein $R_1$ is SH, OH, $CO_2H$ or $CH_2CO_2H$; and
$R^a$ is a $C_5$-$C_{12}$ alkyl group, a $C_5$-$C_{12}$ alkenyl group, a $C_5$-$C_{12}$ alkynyl group, a fluorinated $C_5$-$C_{12}$ alkyl group, a fluorinated $C_5$-$C_{12}$ alkenyl group or a fluorinated $C_5$-$C_{12}$ alkynyl group;
for removing one or more PFASs from an aqueous phase.
In some particular embodiments, the foaming agent of Formula (Ia) or salt thereof is used in an foam fractionation process to remove one or more metal ions and one or more PFASs from the aqueous phase.

In some embodiments of the foaming agent of Formula (Ia), $R_1$ is SH. In other embodiments, $R_1$ is OH. In yet other embodiments, $R_1$ is $CO_2H$. In still other embodiments, $R_1$ is $CH_2CO_2H$. In particular embodiments, $R_1$ is SH, OH or $CO_2H$, especially SH or OH and more especially SH.

In some particular embodiments, $R^a$ is a $C_6$-$C_9$ alkyl group. In some particular embodiments, the foaming agent of Formula (Ia) or salt thereof has a solubility of greater than 0.0001 M in water. In some particular embodiments, the CMC of the foaming agent of Formula (Ia) or salt thereof in the aqueous phase is greater than 0.0001 M. In some particular embodiments, the aqueous phase comprises PFAS-contaminated soil. In some particular embodiments, the aqueous phase is or comprises PFAS-contaminated groundwater.

EXAMPLES

Materials

L-cysteine (97%), octanoyl chloride, octyl bromide, triethylamine, thionylchloride, cadmium standard solutions, calcium chloride dihydrate, sodium hydroxide, THF, methanol, acetone and ethanol were all purchased from Sigma-Aldrich (Australia) and used as received. 1-octanoylbenzotriazole (97%) was purchased from Amadis Chemical (Zhejiang, China). Milli-Q water was used in these experiments.

Abbreviations

| Abbreviation | Explanation |
| --- | --- |
| CMC | Critical Micelle Concentration |
| Cys | Cysteine |
| EA | Elemental Analysis |
| FT-IR | Fourier transform infrared spectroscopy |
| HM | Heavy metal |
| ICP-MS | Inductively Coupled Plasma/Mass Spectrometry |
| MP | Melting Point |
| PFAS | Poly- and perfluoralkyl substances |
| ppm | Parts per million |
| N-octanoyl-cys | N-octanoyl-cysteine |
| N-octyl-cys | N-octyl-cysteine |
| SDS | Sodium dodecyl sulfate |
| SLS | Sodium lauryl sulfate |
| WHO | World Health Organization |

Example 1—Preparation of N-Octanoyl-Cysteine

Comparative Method 1

Scheme 1. Synthesis of N-octanoyl-cys using cysteine and octanoyl chloride

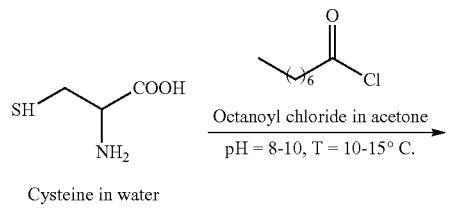

Cysteine in water

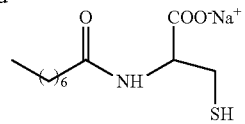

The synthetic route for the synthesis by Comparative method 1 of N-octanoyl-cys is shown in Scheme 1. This method is a water-based method and has been reported previously (M. Taseidifar et al., Environmental Technology & Innovation, 2017, 8, 182-190).

0.06 mol of NaOH and 0.06 mol of L-cysteine were dissolved into 20 mL water at room temperature, followed by adding (dropwise, from a 250 mL separatory funnel) a mixture of 0.08 mol octanoyl chloride and 20 mL acetone, while stirring at 10-15° C. The pH of the solution was kept at about 8-10 by adding sodium hydroxide solution (10%) before adding the mixture of octanoyl chloride and acetone. Then 100 ml acetone was added to the resulting mixture and then the precipitate was filtered and washed with acetone. Finally, the precipitate was recrystallised from ethanol:water (V:V, 50:50). The yield of N-octanoyl-cys from this process was found to be less than 5%, which is too low to support efficient large-scale commercial production.

The melting point of N-octanoyl-cys prepared by this method was determined to be 128'C (using an Electrothermal IA9100 melting apparatus at a heating rate of 1° C. $min^{-1}$).

The CMC of N-octanoyl-cys prepared by this method was determined to be 0.1M. The CMC was determined using a Bench-Top water quality meter, SPER SCIENTIFIC Instrument model 860033 to measure the conductivity and pH of the surfactant solution. The CMC value of the surfactant was measured by plotting conductivity values versus different surfactant concentrations at pH 9 by adding NaOH solution (0.1 mol $L^{-1}$) and 25.0° C. The CMC was obtained as the point of sharp transition in the slope of conductivity with increasing surfactant concentration (data not shown).

Comparative Method 2

Cysteine and octanoic acid were dissolved and refluxed in thionylchloride ($SOCl_2$) to form N-octanoyl cysteine. To trap the formed HCl, the weak base triethylamine (TEA) was used. This route failed.

Comparative Method 3

A solution of cysteine and the base TEA in THF was stirred for 30 min and then a stoichiometric amount of octanoyl chloride was added, followed by a catalytic amount of 4-dimethylaminopyridine (DMAP). Then the mix was refluxed for 18 hours. This method was based on a previous method (J. Phys. Org. Chem., 2017, 30, e3675) reported to be successful for the synthesis of N-acyl phenylalanine and tyrosine. However, in this case octanoyl chloride appeared to react with TEA rather than cysteine (which has a very low solubility in THF). This reaction only produced octanoyl TEA as a white precipitate, which is soluble in acidic solution, whereas, by comparison, octanoyl cysteine should precipitate out.

Comparative Method 4

The 'Schotten Baumann' conditions are based on keeping the reactants (i.e. acyl chloride and amine) in the organic phase (e.g. THF), so that the HCl produced goes into the alkaline water phase—to take up the product acid and so prevents protonation of the amine, which would stop the reaction. Unfortunately, however, the reaction did not proceed after numerous attempts. It is believed that the reaction did not proceed due to the poor solubility of cysteine in the organic phase (THF).

Comparative Method 5

A reaction was carried out in which octanoic acid was used as both a reactant and the solvent. Cysteine was heated in octanoic acid to near reflux at 200° C. to try to obtain N-octanoyl cysteine, with the continuous removal of the produced water. However, this reaction was unsuccessful, presumably because the liquid octanoic acid dehydrated on heating to produce octanoic anhydride and this dominated the reaction, rather than reacting with cysteine, which was in solid form and hard to dissolve in the less-polar solvent.

Comparative Method 6

Ionic liquids (ILs) were investigated in an attempt to increase the yield of N-octanoyl-cys because cysteine should have a high solubility in ILs and octanoyl chloride should not be hydrolysed in this choice of solvent. Two ILs: 1-butyl-3-methylimidazolium triflate, 99% and 1-butyl-3-methylimidazolium hexafluorophosphate, 99%, were supplied from IoLiTec Ionic Liquids Technologies GmbH, Germany. However, use of both ILs failed to produce the desired N-octanoyl-cys, even in a water-free system, using continuous evacuation to remove the HCl product, and with heating to 40° C.

Comparative Method 7

An alternative synthetic route based on a published procedure was trialed (A. R. Katritzky et al. *The Journal of Organic Chemistry,* 2000, 65, 8210-8213). Using THF as solvent, 1-octanoylbenzotriazole failed to deliver the desired the N-octanoylcysteine.

Comparative Method 8

Following a reported method (A. R. Katritzky et al. *The Journal of Organic Chemistry,* 2009, 74, 7165-7167), 2 mmol 1-octanoylbenzotriazole was added to a solution of cysteine (2 mmol) and TEA (2 mmol) in acetonitrile:water (3:1, 8 mL). The mixture was stirred for 2 h at room temperature. However, the reaction failed to produce the desired N-octanoyl-cys product.

Exemplary Method 1

In a typical batch, 1-octanoylbenzotriazole (0.03 mol, 1 eq) was added to a solution of cysteine (0.03 mol, 1 eq) in methanol (20 mL, used as supplied) and stirred for 1 h at room temperature. A white precipitate formed which was collected by filtration and washed with ethanol. The yield was generally in the range of about 95-98%. Scheme 2 shows the synthetic route.

Scheme 2. Synthesis of N-octanoyl cysteine

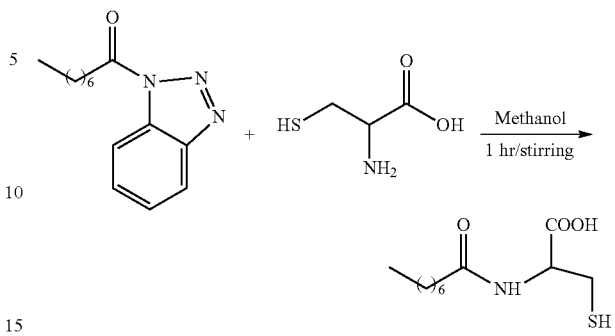

Figure 3:
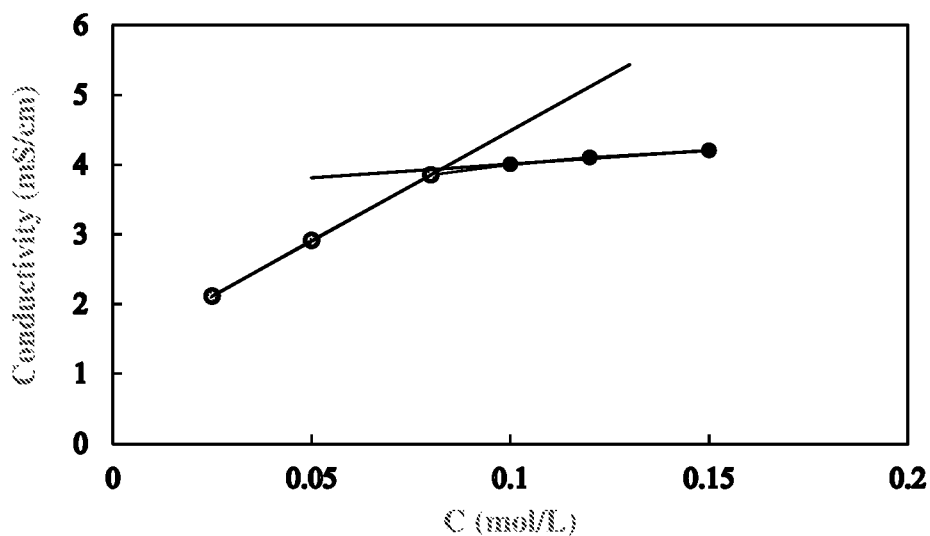
FIG. 3 is a graph showing the electrical conductivities of the surfactant solutions at pH 8, used to calculate the CMC in Example 1.
Figure 4:
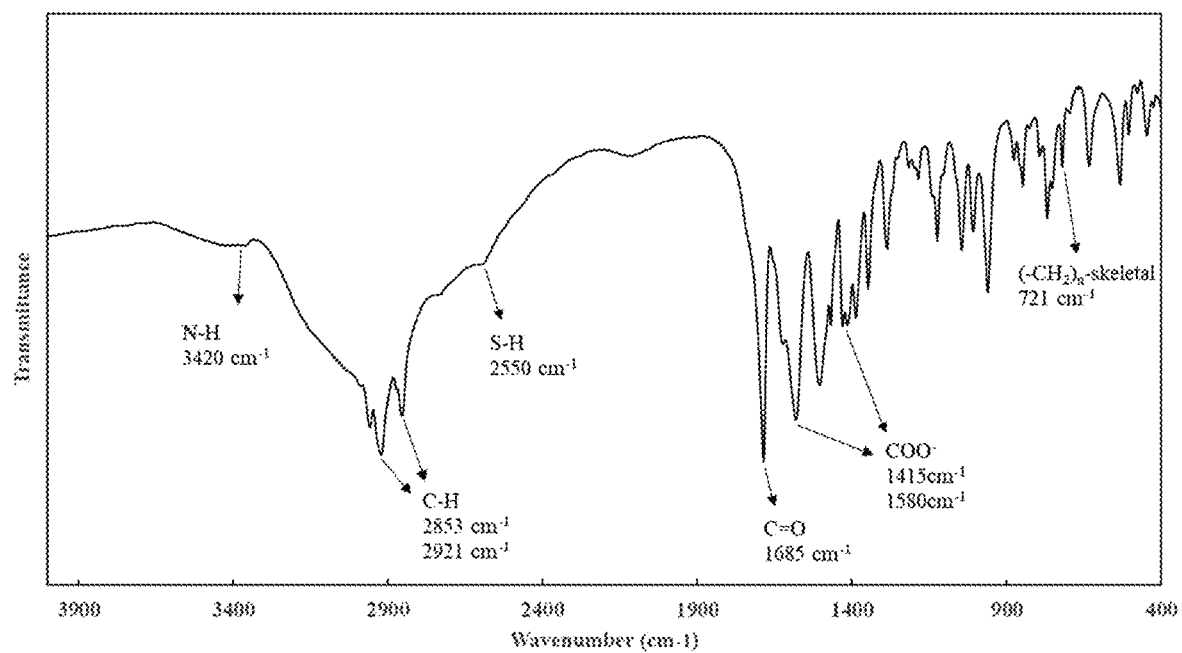
FIG. 4 is au FT-IR spectra of N-octanoyl-cysteine obtained by Exemplary method 1, as described in Example 2.

The CMC of the N-octanoyl-cys surfactant prepared by Exemplary method 1, in Na$^+$ form at pH 8, was determined (as reported above for Comparative method 1 above from measurements of the electrical conductivity with surfactant concentration) to be about 0.09 mol/L, see FIG. 3. The melting point was found to be about 122° C.

Discussion

Using the method reported above for Comparative method 1, based on reacting octanoyl chloride with cysteine in an aqueous environment, a low yield was obtained. The dominant peak in mass spectrum of the product was 353.27 g/mol, which is inconsistent with the calculated value of 247.35 g/mol. The peak corresponding to the desired product was comparatively minor. It is suspected that some portion of the product may have formed the oxidised dimer S—S(i.e. cystine form); especially as there was no peak found that could be ascribed to the —SH group in the Fourier transform infrared spectroscopy (FT-ER) spectrum. It has been reported that cysteine can be oxidised to cystine whilst in a 1 mM solution within few days at pH 7 if exposed to the atmosphere. In our work, the cysteine concentration was kept around 3 M which is relatively concentrated and difficult to become oxidised at normal experimental conditions.

Mass spectroscopy analysis shows that the molecular weight of product obtained by Exemplary method 1 was 248.13 g/mol, consistent with the expected value (in acid form).

The FT-IR spectrum was obtained for octanoyl-cys prepared by Exemplary method 1, which showed values ($v_{max}$, cm$^{-1}$) at 3420 (NH), 2921, 2853 (CH), 2550 (SH), 1685 (C=O), 1580, 1415 (CO$_2^-$) and 721 (—CH$_2$-skeletal). This spectral analysis indicated the presence of NH, SH, COO, CO and CH groups.

An elemental analysis was performed on a sample of N-octanoyl-cys (prepared by Exemplary method 1). The results are presented in Table 1 below.

TABLE 1

Total Elemental Analysis of the synthesised N-octanoyl-cys (prepared by Exemplary method 1) in acid form

| Sample | % C | % H | % N | % S |
|---|---|---|---|---|
| Theory | 53.41 | 8.56 | 5.66 | 12.96 |
| Found | 55.86 | 8.52 | 7.62 | 10.37 |

Example 2—Comparison of N-Octyl Cysteine and N-Octanoyl Cysteine in Ion Flotation Synthesis of N-Octyl Cysteine A similar surfactant, N-octyl cysteine, was synthesised and purified according to a previously reported method (Aslam et al, *ACS Omega*, 2017, 2, 5691-5707). Octyl bromide (0.08 mol) was added to a solution of cysteine (0.06 mol) and thymolphthaleine (as pH indicator) in methanol containing NaOH and stirred at reflux for 5 hours. The presence of the blue colour (from the thymolphthaleine indicator) was monitored to maintain the pH at above about 10. After 5 h, the pH was adjusted to 5 by adding 1M HCl and then the white-coloured precipitate was filtered and washed with a mixture of acetone and water. Finally, the precipitate was crystallised two times in a mixture of ethanol:water (V:V, 50:50). Scheme 3 shows the synthetic route.

Scheme 3. Reaction to obtain N-octyl cysteine (N-octyl-cys) surfactant.

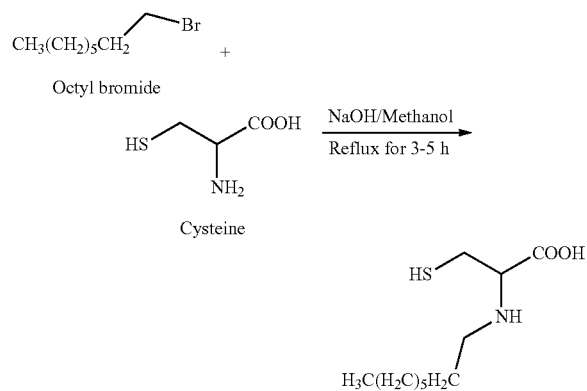

The same protocols as described above were used to determine the CMC and melting point of the twice-recrystallised N-octyl-cysteine surfactant. The values measured were 0.1M and 145° C., respectively. These values are consistent with literature values.

Ion Flotation System—Cd

In a model experiment, 0.01M of the N-octanoyl-cys surfactant was dissolved (with heating around 65° C. while stirring) in a 5 mg $L^{-1}$ solution (i.e. 5 ppm) of Cd containing 0.1 M NaOH and finally made up to 100 ml using Milli-Q water, with the pH of around 8.

The solution was then poured into a column (with 30 cm height and 3 cm diameter) while a 2 L/min flow of air gas was passed through it with air pump (Hiblow HP40, Philippines). Two samples were taken after each of 30 and 60 minutes from around 2 cm top of the sinter, and the Cd concentrations of each sample was determined by ICP-MS analysis. The upper-outlet foam was also collected in a waste container using an outlet tube. A schematic diagram of the column setup is shown in FIGS. 1 and 2.

The same procedure was used with the N-octyl-cys surfactant in the flotation experiment, but where the pH of the solution was increased to 12, to enable this surfactant to successfully produce a foam (this difference is discussed later).

The results of the removal of 5 mg $L^{-1}$ of Cd solution using the N-octanoyl-cys and the N-octyl-cys surfactants presented in Table 2 show that N-octanoyl-cys surfactant is noticeably more efficient for removing Cd.

TABLE 2

Ion flotation results for 100 mL of 5 mg $L^{-1}$ Cd solution using N-octanoyl-cys and N-octyl-cys surfactants with air inlet gas. In the brackets, the relative standard deviations (RSD) for concentrations are given. ($C_{surfactant}$ = 0.01M)

| Surfactant (prepared by) | Operating pH | Concentration of Cd after 30 min (RSD %) | Concentration of Cd after 60 min (RSD %) | Adsorption (%) After 60 min |
|---|---|---|---|---|
| N-octanoyl-cys (Comparative method 1) | 8 | 0.269 mg $L^{-1}$ (14.38) | 0.041 mg $L^{-1}$ (36.63) | 99.2 |
| N-octanoyl-cys (Exemplary method 1) | 8 | 0.43 mg $L^{-1}$ (19.5) | 0.01 mg $L^{-1}$ (23.8) | 99.8 |
| N-octanoyl-cys (Exemplary method 1) | 12 | 4.928 mg $L^{-1}$ (0.77) | 4.383 mg $L^{-1}$ (5.8) | 12.3 |
| N-octyl-cys (described above) | 12 | 4.727 mg $L^{-1}$ (3.14) | 4.263 mg $L^{-1}$ (4.29) | 14.2 |

A likely explanation for the better performance of the N-octanoyl-cys surfactant compared with the N-octyl-cys surfactant in the flotation experiments is that protonation of the amide group in the N-octanoyl-cys surfactant only occurs at low pH (i.e. in strong acid), since the pKa is around −0.5. However, the amine group in the N-octyl-cys surfactant more readily protonated, having a pKa value of about 10.7. Hence, at medium pH (of around 8) the N-octyl-cys surfactant may be protonated, forming the observed agglomeration phase. Increasing pH to 12 allows the N-octyl-cys surfactant to dissolve and can then foam in the flotation system. By comparison, at a pH of around 8, the N-octanoyl-cys surfactant readily foams.

Scheme 4. Resonance contributor of the amide group in N-octanoyl-cys means that sharing the electrons on the nitrogen deters its protonation.

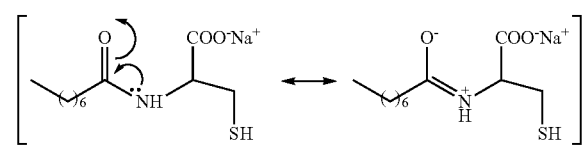

Figure 6:
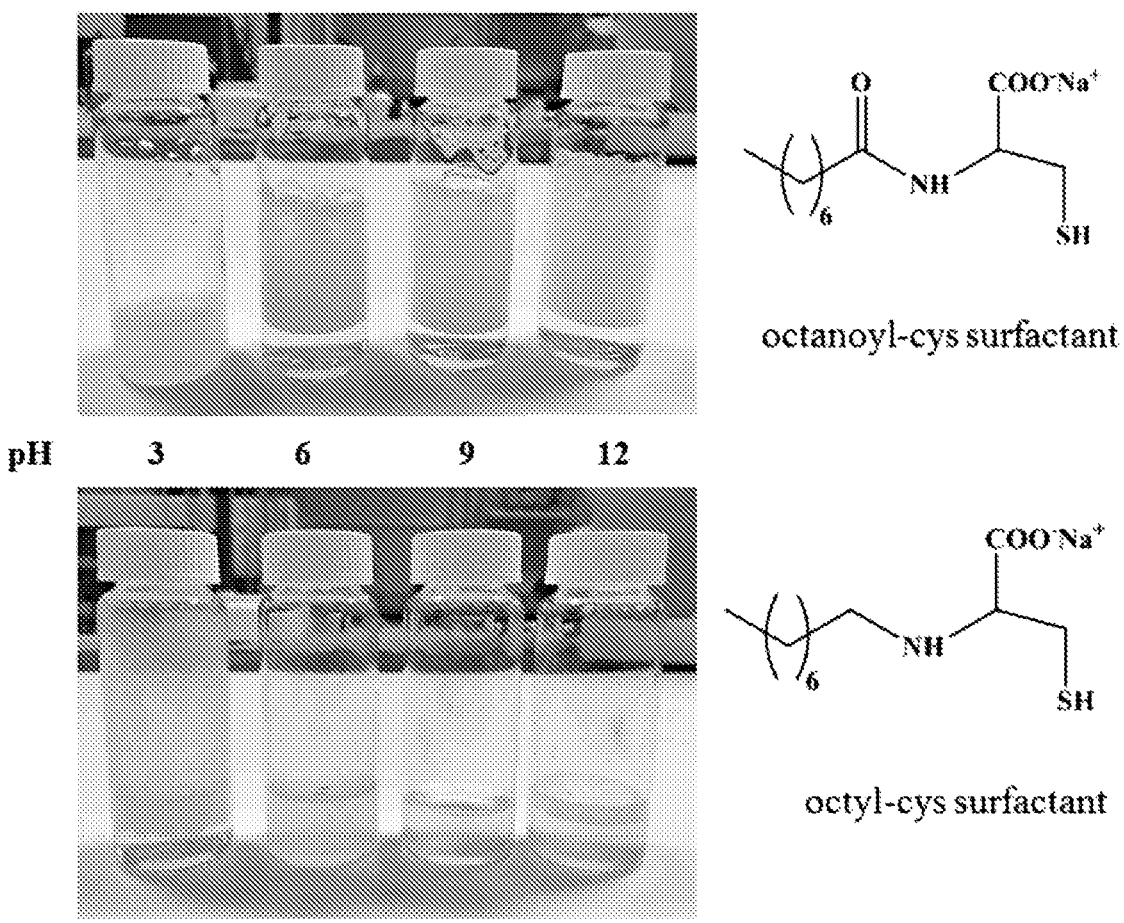
FIG. 6 is a pair of photos from the foaming test described in Example 2; the first photo (upper) is a photo of N-octanoyl cysteine solutions at: pH 3 (far left), pH 6 (middle left), pH 9 (middle right) and pH 12 (far right) and the second photo (lower) is a photo of N-octyl cysteine solutions at: pH 3 (far left), pH 6 (middle left), pH 9 (middle right) and pH 12 (far right). (Csurfactant=0.01M and the pH adjusted with 0.1 M NaCl).
Figure 7:
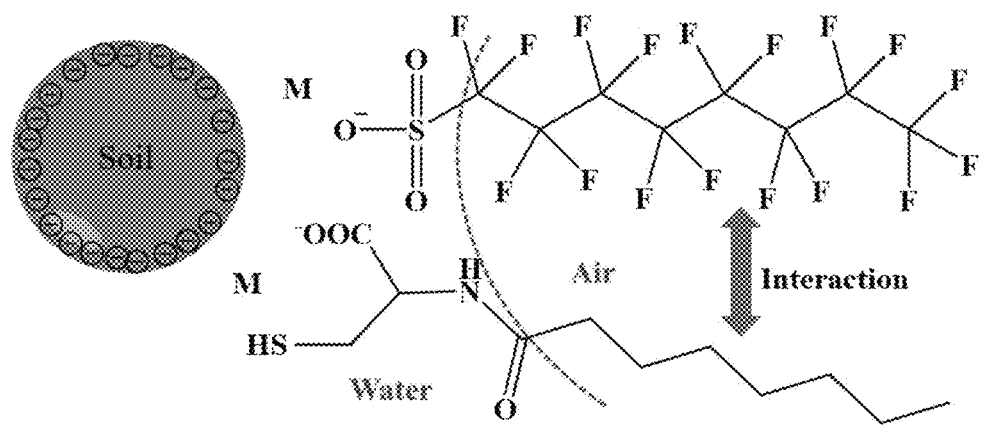
FIG. 7 is a schematic diagram of the region in and adjacent to the surface of a bubble showing: a possible binding motif between a negatively charged soil particle, a metal ion and a PFAS (upper left); a possible binding motif between a negatively charged soil particle, a metal ion and a foaming agent of Formula (Ia) (lower left); and a possible interaction between the hydrophobic regions of a PFAS and a foaming agent of Formula (Ia) (right). Such a scenario may, for example, exist in the waste container depicted in FIG. 2.

Foaming tests of the two surfactants (N-octanoyl-cys and N-octyl-cys) show that N-octanoyl-cys surfactant starts foaming at pH~6 while for the N-octyl-cys surfactant foaming point was obtained to be more than pH 12 (see FIG. 6).

The wide active pH range for the N-octanoyl-cys surfactant is also useful for soil remediation because rainwater (pH of ~5.7) has a lower pH than typical river water (pH of ~8) and during heavy rainfall the soil can become saturated and the water then has a reduced pH, sometimes in the pH 6-7 range. Hence, this surfactant may still be used for soil foam fractionation cleaning under these flooded conditions.

Ion Flotation System—Ca

In the second series of ion flotation experiments, N-octanoyl-cys surfactant (obtained by Exemplary method 1) was used for removing calcium ions using air in the ion flotation process. Table 3 shows the analysis of the ion flotation solutions using ICP-MS. The results show that the N-octanoyl-cys had a high performance in removing calcium, at high level of 97% in the ion flotation process. This surfactant successfully reduced the 5 mg $L^{-1}$ calcium content to a level lower than 0.13 mg $L^{-1}$ in a single stage, physicochemical process. The same procedure using N-octyl-cys surfactant had a removal efficiency of 14% at pH 12.

TABLE 3

Flotation results using an air bubbles for 100 mL of 5 mg L$^{-1}$ calcium using N-octanoyl-cys and N-octyl-cys surfactants ($C_{calcium}$ = 5 mg L$^{-1}$ and $C_{surfactant}$ = 0.01M)

| Surfactant | pH | C(mg L$^{-1}$) (RSD %) After 30 min | C(mg L$^{-1}$) (RSD %) After 60 min | Adsorption (%) After 60 min |
|---|---|---|---|---|
| N-octanoyl-cys | 8 | 0.72 (42.02) | 0.13 (29.01) | 97.3 |
| N-octyl-cys | 12 | 4.89 (0.87) | 4.27 (3.31) | 14.6 |

Observations Concerning Examples 1 and 2

In view of the above examples, the surfactant N-octanoyl-cys proved itself as a useful surfactant which has excellent metal-binding and foaming properties over a wide range of pH values. It is also likely to be environmentally acceptable, as it readily breaks down into octanoic acid and cysteine, both of which have little to no toxicity concerns and are even present in some foods. For example, octanoic acid is found naturally in the milk of various mammals and as a minor constituent of coconut oil and palm kernel oil. The chain length is also similar to many common PFAS compounds and may offer co-surfactant and chelation properties useful for soil treatment using foam fractionation and/or foam flotation. N-octanoyl-cys may be biodegraded by enzymes to produce natural products. N-octanoyl-cys surfactant shows promising commercial applications in various industries, including detergents, cleaning products, toothpaste and also as natural soaps.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The claims defining the invention are as follows:

1. A method of removing one or more per- and polyfluoroalkyl substances (PFASs) from an aqueous phase comprising one or more PFASs, the method comprising dissolving in the aqueous phase a foaming agent of Formula (Ia):

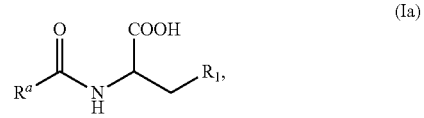

or a salt thereof,
wherein $R_1$ is SH, OH, $CO_2H$ or $CH_2CO_2H$; and
$R^a$ is a $C_5$-$C_{10}$ alkyl group, a $C_5$-$C_{10}$ alkenyl group, a $C_5$-$C_{10}$ alkynyl group, a fluorinated $C_5$-$C_{10}$ alkyl group, a fluorinated $C_5$-$C_{10}$ alkenyl group or a fluorinated $C_5$-$C_{10}$ alkynyl group;
forming a foam from the aqueous phase and a gas; and separating the foam from the aqueous phase.

2. The method according to claim 1, wherein $R_1$ is OH or SH.

3. The method according to claim 2, wherein $R_1$ is SH.

4. The method according to claim 1, wherein $R^a$ is a $C_6$-$C_9$ alkyl group.

5. The method according to claim 1, wherein the foaming agent is in salt form.

6. The method according to claim 1, wherein the foaming agent of Formula (Ia) or salt thereof has a solubility of greater than 0.0001 M in water.

7. The method according to claim 1, wherein the critical micelle concentration (CMC) of the foaming agent of Formula (Ia) or salt thereof in the aqueous phase is greater than 0.0001 M.

8. The method according to claim 1, wherein the concentration of the foaming agent of Formula (Ia) or salt thereof in the aqueous phase is from about 0.01 mM to about 2 M.

9. The method according to claim 1, wherein the concentration of the foaming agent of Formula (Ia) or salt thereof in the aqueous phase is from about 0.0001 M to about 2 M.

10. The method according to claim 1, wherein the one or more PFASs comprises at least one PFAS capable of binding to a multivalent metal ion.

11. The method according to claim 1, wherein the aqueous phase has a pH within the range of from about pH 4 to about pH 12.

12. The method according to claim 1, wherein the aqueous phase comprises one or more metal ions selected from $Ca^{2+}$, $Mg^{2+}$, $Al^{3+}$ and $Fe^{3+}$.

13. The method according to claim 1, wherein the aqueous phase comprises PFAS-contaminated soil or PFAS-contaminated groundwater.

* * * * *